United States Patent [19]

Suzuki et al.

[11] Patent Number: 5,152,783
[45] Date of Patent: Oct. 6, 1992

[54] ANTITHROMBOGENIC MATERIAL

[75] Inventors: Yoshiaki Suzuki, Tokyo; Masahiro Kusakabe, Kanagawa; Iwaki Masaya, Saitama; Kiyoko Kusakabe, Tokyo, all of Japan

[73] Assignees: Sony Corporation, Tokyo; Rikagaku Kenkyusho, Saitama, both of Japan

[21] Appl. No.: 570,614

[22] Filed: Aug. 21, 1990

[30] Foreign Application Priority Data

Sep. 28, 1989 [JP] Japan .................................. 1-250523

[51] Int. Cl.$^5$ .............................................. A61F 2/06
[52] U.S. Cl. .......................................... 623/1; 623/11; 623/12; 623/66; 604/266; 600/36; 427/2
[58] Field of Search .................. 623/1, 11, 12, 66, 901; 604/266; 606/76, 153, 231; 600/36; 427/2

[56] References Cited

U.S. PATENT DOCUMENTS

| | | | |
|---|---|---|---|
| 3,808,113 | 4/1974 | Okamura et al. | 623/1 |
| 3,903,891 | 9/1975 | Brayshaw | 606/27 |
| 3,955,012 | 5/1976 | Okamura et al. | 623/66 |
| 4,718,905 | 1/1988 | Freeman | 623/6 |
| 4,851,009 | 7/1989 | Pinchuk | 623/1 |

Primary Examiner—Paul Prebilic
Attorney, Agent, or Firm—Philip M. Shaw, Jr.

[57] ABSTRACT

An antithrombogenic material having its surface modified by ion implantation is disclosed. This antithrombogenic material may, for example, be a silicone material which has its surface modified by introducing functional groups on its surface by ion implantation. The material exhibits improved compatibility to blood due to introduction of the functional groups by ion implantation and the doping effect of the implanted elements.

15 Claims, 3 Drawing Sheets

ANTITHROMBOGENIC MATERIAL

BACKGROUND OF THE INVENTION

This invention relates to an antithrombogenic material employed in artificial biocompatible material, such as an artificial blood vessel, or in medical equipment brought into contact with blood.

Recently, with the progress in medical technology, evolution of artificial or prosthetic organs having the function similar to that of a living body is progressing. For example, a medical equipment through which the blood from the living body is caused to flow transiently, such as an artificial dialysis system, or artificial organs, such as artificial blood vessel or artificial heart, are being put to practical usage.

Among the properties required of these medial equipment and artificial organs are biocompatibility and, above all, antithrombogenicity, especially at the portions thereof directly contacted with the blood. Should the artificial material exhibit low antithrombogenic in these portions, platelets tend to be accumulated to coagulate the blood to form blood clots, that is thrombus, which inhibits blood stream or which is moved with the blood stream to cause cerebral thrombosis, myocardial infarction or pulmonary infarction. Thus the formation of blood clots represents a serious problem to the human body.

Under these circumstances, various antithrombogenic materials have been evolved, such as polyurethane-silicone block polymers, heparinated high molecular materials, hydroxy ethyl methacrylate-styrene block polymer, urokinase immobilized high polymer material or plasma treated high molecular weight materials, for use in various fields of applications.

However, the first to fourth of these antithrombogenic material are prepared by chemical synthesis through various steps such as material refining or separation for synthesis with resulting inconveniences in productivity, equipment investments and costs.

The fifth material, which may be produced by physical processes, has a drawback that it presents a non-homogeneous treatment surface.

In short, the conventional antithrombogenic materials leave much to be desired in that the manufacture process is complicated or the product of a uniform quality cannot be produced without considerable difficulties.

OBJECTS AND SUMMARY OF THE INVENTION

It is therefore an object of the present invention to provide an antithrombogenic material which may be produced by a simple technique and which exhibits superior antithrombogenic.

The antithrombogenicity material of the present invention is characterized in that its surface has been modified by ion implantation and in that it consists of a silicone material which has its surface modified by introducing functional groups on its surface by ion implantation. With the antithrombogenic material of the present invention, compatibility to blood may be markedly improved by the introduction of the functional groups by ion implantation and by the doping effect of the implanted elements.

DESCRIPTION OF THE PREFERRED EMBODIMENTS

Figure 1:
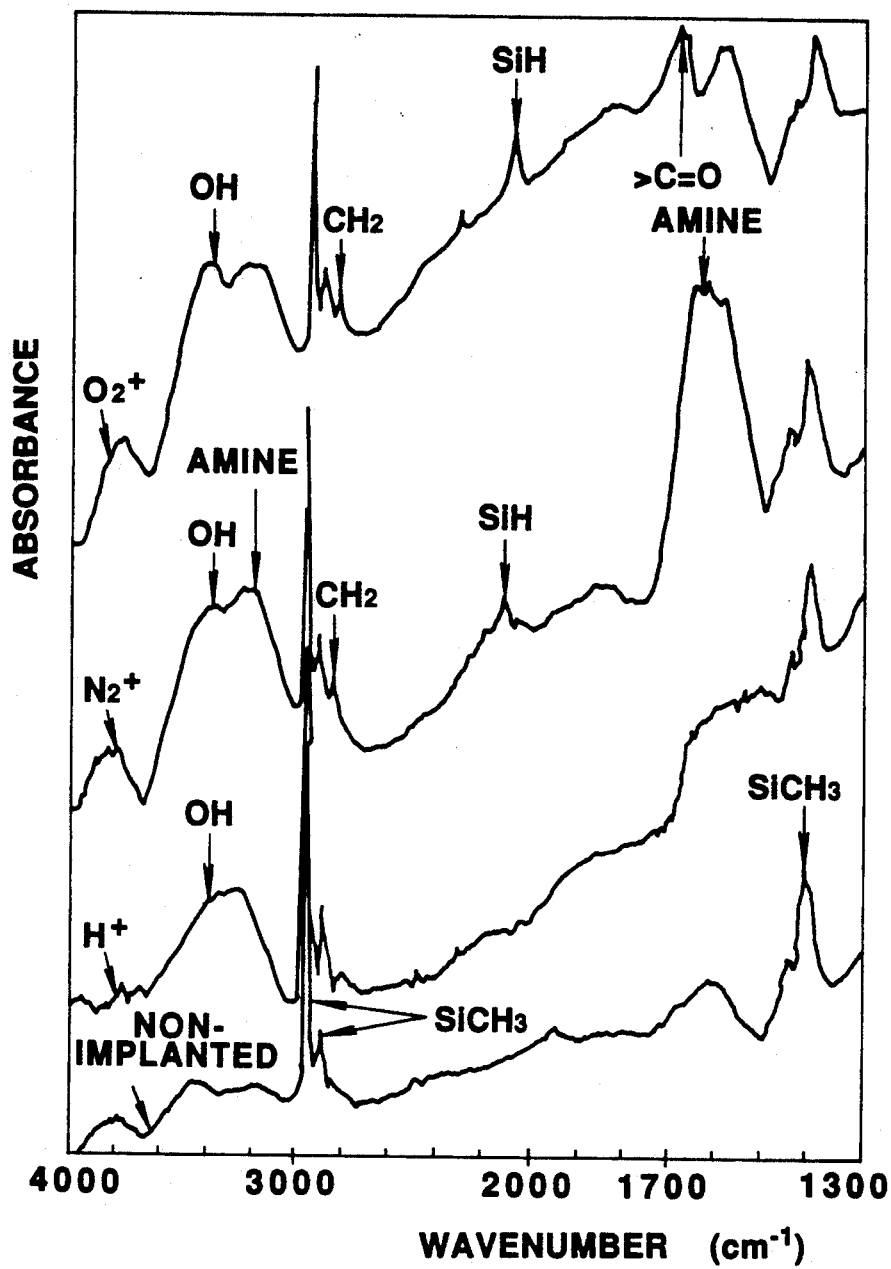
FIG. 1 shows the Fourier Transform Infrared Spectrometry Attenuated Total Reflection (FT-IR-ART) spectrum on the silicone surface layer implanted with ions.

The present inventors have conducted eager searches for accomplishing the above object and reached the conclusion that ion implantation is highly effective in improving antithrombogenic.

The antithrombogenicity material of the present invention has been fulfilled on the basis of the above finding and is characterized in that the material has its surface modified by ion implantation.

Although there is no limitation to the artificial materials employed in the present invention, high molecular material, above all a silicone material is most preferred, and an antithrombogenicity material having superior compatibility with blood may be produced by modifying the silicone material through ion implantation.

Although the ion species such as $O_2^+$, $H^+$ and $N_2^+$ are preferred for implantation, such ions as $He^+$, $C^+$, $N^+$, $O^+$, $Ne^+$, $Na^+$, $Ar^+$ or $K^+$ may also be employed.

Although the amount of ions implanted and the energy for acceleration may be optically selected in dependence upon the usage or the species of the ions, they are usually selected to be in the range of about $1 \times 10^{12}$ to $3 \times 10^{17}$ cm$^{-2}$ and in the range of tens to hundreds of keVs, respectively.

The possible reason for the improved antithrombogenic due to ion implantation is the introduction of a various functional groups into the artificial material, such as the silicone material, by the irradiation of the ion beams. The following Table 1 shows the species of functional groups generated in the silicone as a result of the ion implantation. Although OH groups are produced by implantation of any ion species, it is not clear if this is directly related with the antithrombogenic.

Although the doping effect of the implanted elements may be taken into consideration, it may be presumed that the introduction of the superficial functional groups and the doping are operating synergistically.

TABLE 1

| ion species | introduced functional groups | | |
|---|---|---|---|
| $H^+$ | SiOH, | | |
| $He^+$ | SiOH, SiH | | |
| $C^+$ | SiOH, SiH, | $>C=O$ | |
| $N^+$ | SiOH, SiH, | amine | |
| $O^+$ | SiOH, SiH, | $>C=O$ | |
| $Ne^+$ | SiOH, SiH, | | |
| $Na^+$ | SiOH, SiH, $CH_2$ | carboxylate | |
| $N_2^+$ | SiOH, SiH, $CH_2$ | amine | |
| $O_2^+$ | SiOH, SiH, $CH_2$ | $>C=O$ | |
| $K^+$ | SiOH, $CH_2$ | 1560 cm$^{-1}$ | |
| $Ar^+$ | SiOH, SiH, $CH_2$ | | |

The present invention will be explained on the basis of concrete experimental results.

In the present experiment, $H^+$, $O_2^+$ and $N_2^+$ were implanted in a silicone intended for medical use to test the compatibility thereof with the blood.

Sample

A silicone sheet for medical use, produced by the Toshiba Silicone Co. Ltd., was used as the material to be modified by ion implantation.

This silicone sheet has been prepared by thermally vulcanization cure of a polymer having a siloxane linkage Si-O in its main chain and side methyl chains $CH_3$, as shown in the following structural formula, in the presence of a Pt catalyst:

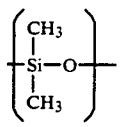

Ion Implantation

Using a 200 kV ion implantation unit, prepared by Rikagaku Kenkyusho, $H^+$, $O_2^+$ and $N_2^+$ ions were implanted at an acceleration energy of 150 keVs. The ion beam current of not more than 1 $\mu A/cm^2$ was used to suppress a temperature rise in the sample. The amount of ions implanted was selected to be $2\times10^{17}$ $cm^{-2}$ and $1\times10^{17} cm^{-2}$, for the ion species of $H^+$ and $O_2^+$ or $N_2^+$, respectively.

Chemical Properties of Ion Implantation Samples

The samples irradiated with the ion beam undergoes a variety of physical and chemical changes. By way of physical and chemical evaluation, measurements were made of the amounts of decomposition of the siloxane linkages and methyl groups as well as the superficial functional groups by the Fourier Transform Infrared Spectrometry Attenuated Total Reflection (FT-IT-ATR) method.

FIG. 1 shows a spectrum by FT-IR-ATR of a sample into which ions have not been implanted and a sample into which ions have been implanted for the wavelength range of 1300 to 4000 $cm^{-1}$.

As may be seen from FIG. 1, various functional groups may be observed to have been produced on the surface layers of the samples in which ions have been implanted. Above all, OH group was yielded as a result of $H^+$ implantation, OH and SiH groups and amine were produced as a result of $N_2^+$ implantation and OH, $CH_2$, SiH and carbonyl groups were produced as a result of $O_2^+$ implantation. Most outstanding were the yielding of the amine and carbonyl groups by $N_2^+$ implantation $O_2^+$ implantation, respectively.

Evaluation by Antithrombogenic of the Ion-Implanted Samples

A rat was used as a laboratory animal. After platelets marked with a radioactive isotope (In-$^{111}$-tropolone) were intravenously administered to the rat under anesthetization, the ion-implanted sample was introduced into the superior vena cava via common carotid and retained there for two days.

The rat was then killed by loss of blood on heparin administration and the ion-implanted sample as well as the main organs were extracted. Using a scintillation counter, the radioactivity, i.e. the count ratio with respect to blood per unit weight, was measured of these samples and the main organs and the state of accumulation (formation of blood clots) was observed. Marking of the rat's platelets by In-$^{111}$-tropolone was performed in accordance with the Dewanjee et al's method.

Figure 2A:
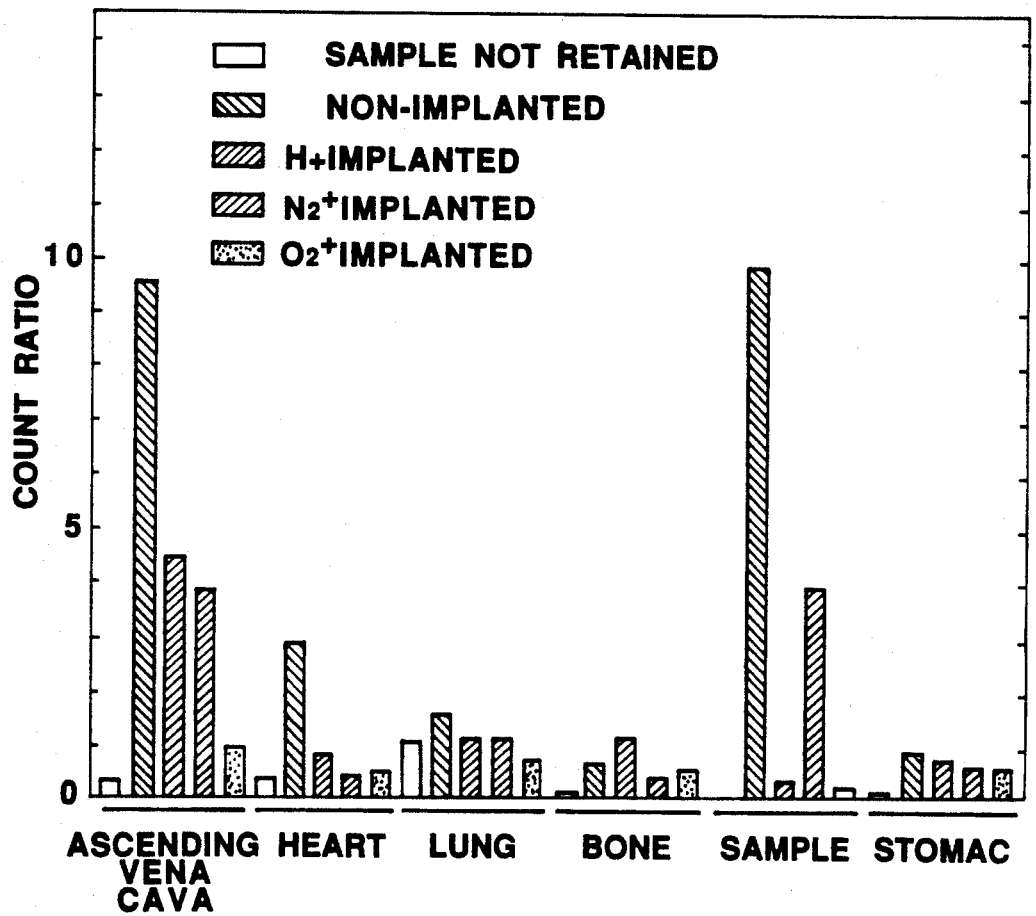
FIGS. 2A and 2B are charts showing the degree of platelet accumulation on the main organs of rats supplied with ion-implanted samples and on the samples in terms of the count ratio as measured with a scintillation counter.
Figure 2B:
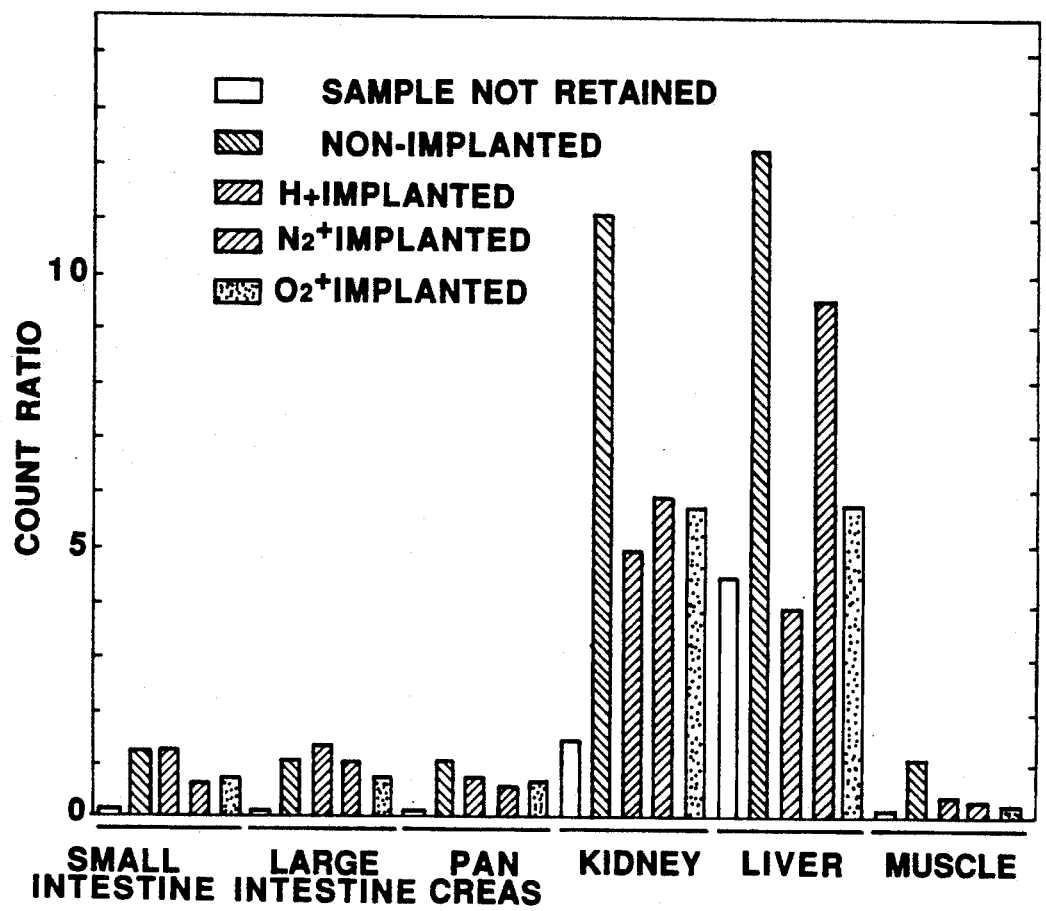

FIGS. 2A and 2B show the count ratio of the In-$^{111}$-tropolone-platelet samples and the organs in rats not supplied with artificial blood vessel samples in the blood, rats supplied with artificial blood samples not implanted with ions, and rats supplied with artificial blood vessel samples implanted with ions, with respect to the samples and the organs.

With the rats supplied with artificial blood vessel samples not implanted with ions, platelet accumulation in the superior vena cava, hearts, samples, kidneys and livers was increased acutely as compared to that with the rats not supplied with the artificial blood vessel samples.

Conversely, with rats supplied with blood vessel samples in which $H^+$ ions were implanted, platelet accumulation on the sample surface was decreased markedly. The same decreasing tendency was also noticed at the superior vena cava, hearts, kidneys and livers.

With rats supplied with artificial blood vessel samples in which $N_2^+$ ions were implanted, platelet accumulation was decreased at the superior vena cava, samples, hearts, kidneys and livers, whereas, with rats supplied with artificial blood vessel samples in which $O_2^+$ ions were implanted, platelet accumulation was decreased markedly in samples and superior vena cava and decreased in the hearts, kidneys and livers.

It may be seen from above that, with artificial blood vessel samples implanted with various ion species, platelet accumulation is markedly decreased on the sample surface with $H^+$ ion implantation while it is markedly decreased not only on the sample but also in the superior vena cava with $O_2^+$ implantation. When platelet accumulation is decreased on the sample surface, it tends to be decreased in hearts, kidneys or livers as well, whereas, when platelet accumulation is decreased on the sample surface and in the superior vena cava, it is similarly decreased in the main organs.

Among the effects of retention of an artificial material in a living body are the formation of thrombus on the artificial material itself and platelet accumulation in the intrafiler organs. With $H^+$ implantation, thrombus on the sample surface is suppressed, and platelet accumulates on the blood vessel wall. However, as compared to the artificial blood vessel sample in which $N_2^+$ ions are implanted, platelet accumulation on the blood vessel wall occurs to the same extent, whereas platelet accumulation on the liver occurs to a lesser extent. It may be seen that platelet accumulation on the intrafiler organs may be decreased due to the lesser damage inflicted on the platelets by contact with the artificial blood vessel samples. It may also be seen that the more the extent of suppression of platelet accumulation on the sample surface, the more the extent of suppression of platelet accumulation on the liver and the lesser the extent of damages inflicted on the platelets. Among the ion species employed in the present experiments, $O_2^+$ ions are most effective on suppressing platelet accumulation.

It is seen from above that the antithrombogenic material of the present invention exhibits superior compatibility to blood and affects the spleen, kidney or liver to a markedly lesser extent. This means that the damages done to the platelets within the living body have been decreased, which is of critical significance in not disturbing the living body system.

The antithrombogenic material of the present invention is manufactured by a surface treatment technique under thermally unbalanced conditions without employing chemical synthesis, so that no complicated process is necessitated with obvious advantages in productivity.

As compared to the manufacture by plasma processing, the direct effect is achieved while the uniformity and controllability are also excellent, since the interaction between the ion beam and the solid material is resorted to.

As compared to various conventional antithrombogenic materials, the antithrombogenic materials of the present invention may be manufactured easily by surface modification, and antithrombogenic may be advantageously improved by application to existing medical appliances.

What is claimed is:

1. A biocompatible antithrombogenic device comprising:
   a silicone material having an external surface; and
   ions selected from the group consisting of $H^+$, $He^+$, $Ne^+$, $Na^+$, $O_2^+$, $K^+$, $Ar^+$ and mixtures thereof implanted on the surface of the silicone material in sufficient quantity to substantially suppress platelet accumulation when exposed to blood.

2. A biocompatible antithrombogenic device comprising:
   a silicone material having an external surface; and
   functional groups selected from the group consisting of SiOH, SiH, $CH_2$, CO, $NH_2$, $CO_2H$ and mixtures thereof on the external surface of the silicone material in sufficient quantity to substantially suppress platelet accumulation when exposed to blood.

3. The antithrombogenic device according to claim 2 wherein the functional groups are selected from the group consisting of CO, $NH_2$ and mixtures thereof.

4. The antithrombogenic device according to claim 1 wherein the ions are selected from the group consisting of $H^{30}$, $O_2^+$ and mixtures thereof.

5. The antithrombogenic device material according to claim 2 wherein the silicone material is a polymer having the formula

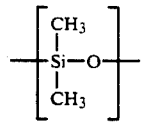

6. The antithrombogenic device according to claim 4 wherein the ions are $O_2^+$ and CO functional groups are present on the silicone material surface.

7. The antithrombogenic device according to claim 4 wherein the ions are $H^+$ and SiOH functional groups are present on the silicone material surface.

8. The antithrombogenic device according to claim 3 wherein the functional groups are $NH_2$, SiOH or SiH and further comprising $N_2^+$ ions are implanted on the silicone material surface.

9. The antithrombogenic device according to claim 1 wherein the ions are $He^+$ and on the silicone material surface SiOH or SiH functional groups are present.

10. The antithrombogenic device according to claim 2 wherein the functional groups are SiOH, SiH or CO and further comprising $C^+$ ions are implanted on the silicone material surface.

11. The antithrombogenic device according to claim 1 wherein the ions are $Ne^+$ and SiOH and SiH functional groups are present on the silicone material surface.

12. The antithrombogenic device according to claim 1 wherein the ions are $Na^+$ and SiOH, SiH, $CH_2$ and $CO_2H$ functional groups are present on the silicone material surface.

13. The antithrombogenic device according to claim 1 wherein the ions are $K^+$ and SiOH and $CH_2$ functional groups are present on the silicone material surface.

14. The antithrombogenic device according to claim 1 wherein the ions are $Ar^+$ and SiOH, SiH and $CH_2$ functional groups are present on the silicone material surface.

15. The antithrombogenic device of claim 1 wherein the concentration of ions implanted on the silicone material surface is approximately between $1 \times 10^{12}$ and $3 \times 10^{17}$ per cm$-2$.

* * * * *